United States Patent
Schneidereit et al.

(10) Patent No.: US 9,925,029 B2
(45) Date of Patent: Mar. 27, 2018

(54) METHOD OF MANUFACTURING A SURGICAL IMPLANT HAVING A MARKING

(71) Applicant: Johnson & Johnson Medical GMHB, Somerville, NJ (US)

(72) Inventors: Jenifer Schneidereit, Hamburg (DE); Boris Batke, Lubeck (DE); Barbara Schuldt-Hempe, Bad Bramstedt (DE)

(73) Assignee: Johnson & Johnson Medical GMBH, Norderstedt (DE)

( * ) Notice: Subject to any disclaimer, the term of this patent is extended or adjusted under 35 U.S.C. 154(b) by 245 days.

(21) Appl. No.: 14/832,095

(22) Filed: Aug. 21, 2015

(65) Prior Publication Data

US 2016/0106530 A1 Apr. 21, 2016

(30) Foreign Application Priority Data

Oct. 15, 2014 (DE) .......................... 10 2014 015 179

(51) Int. Cl.
| | | |
|---|---|---|
| A61B 17/08 | (2006.01) | |
| A61F 13/15 | (2006.01) | |
| B29C 53/00 | (2006.01) | |
| B29C 65/00 | (2006.01) | |
| B32B 7/08 | (2006.01) | |
| B32B 3/04 | (2006.01) | |
| B32B 37/00 | (2006.01) | |
| B32B 38/04 | (2006.01) | |

(Continued)

(52) U.S. Cl.
CPC .... *A61F 2/0063* (2013.01); *A61F 2230/0017* (2013.01); *A61F 2240/001* (2013.01); *A61F 2250/0097* (2013.01); *B29C 65/02* (2013.01); *B29C 65/62* (2013.01); *B29C 65/72* (2013.01); *D10B 2509/08* (2013.01)

(58) Field of Classification Search
CPC ............ A61F 2/0063; A61F 2002/0068; A61F 2250/0097; A61F 2240/001; D10B 2509/08; B29C 65/02; B29C 65/62; B29C 65/72; B29C 66/472; B29C 66/4722
USPC ......... 156/60, 91, 92, 93, 94, 196, 216, 217, 156/221, 227, 250, 267, 289, 297, 299, 156/300, 308.2, 309.6; 606/148, 151; 600/37
See application file for complete search history.

(56) References Cited

U.S. PATENT DOCUMENTS

| | | | |
|---|---|---|---|
| 8,579,922 B2 * | 11/2013 | Glick ............... | A61B 17/06166 606/148 |
| 2005/0288691 A1 * | 12/2005 | Leiboff .................. | A61F 2/0063 606/151 |

(Continued)

FOREIGN PATENT DOCUMENTS

| | | |
|---|---|---|
| DE | 102013004486 | 9/2004 |
| EP | 1439796 | 4/2010 |

*Primary Examiner* — Philip Tucker
*Assistant Examiner* — Brian R Slawski
(74) *Attorney, Agent, or Firm* — E. Richard Skula

(57) ABSTRACT

In a method of manufacturing a surgical implant, a flexible areal basic structure having a first face and a second face is provided. At least one linear marking thread is placed, in a floating manner, onto one of the faces of the basic structure and mechanically fixed (e.g. by stitching) to the basic structure at a first location and at a second location which are spaced from each other. Thereafter, the linear marking thread is thermally fixed to the basic structure in an area between the first location and the second location by a melt-fusing process.

15 Claims, 3 Drawing Sheets

Figure 1:
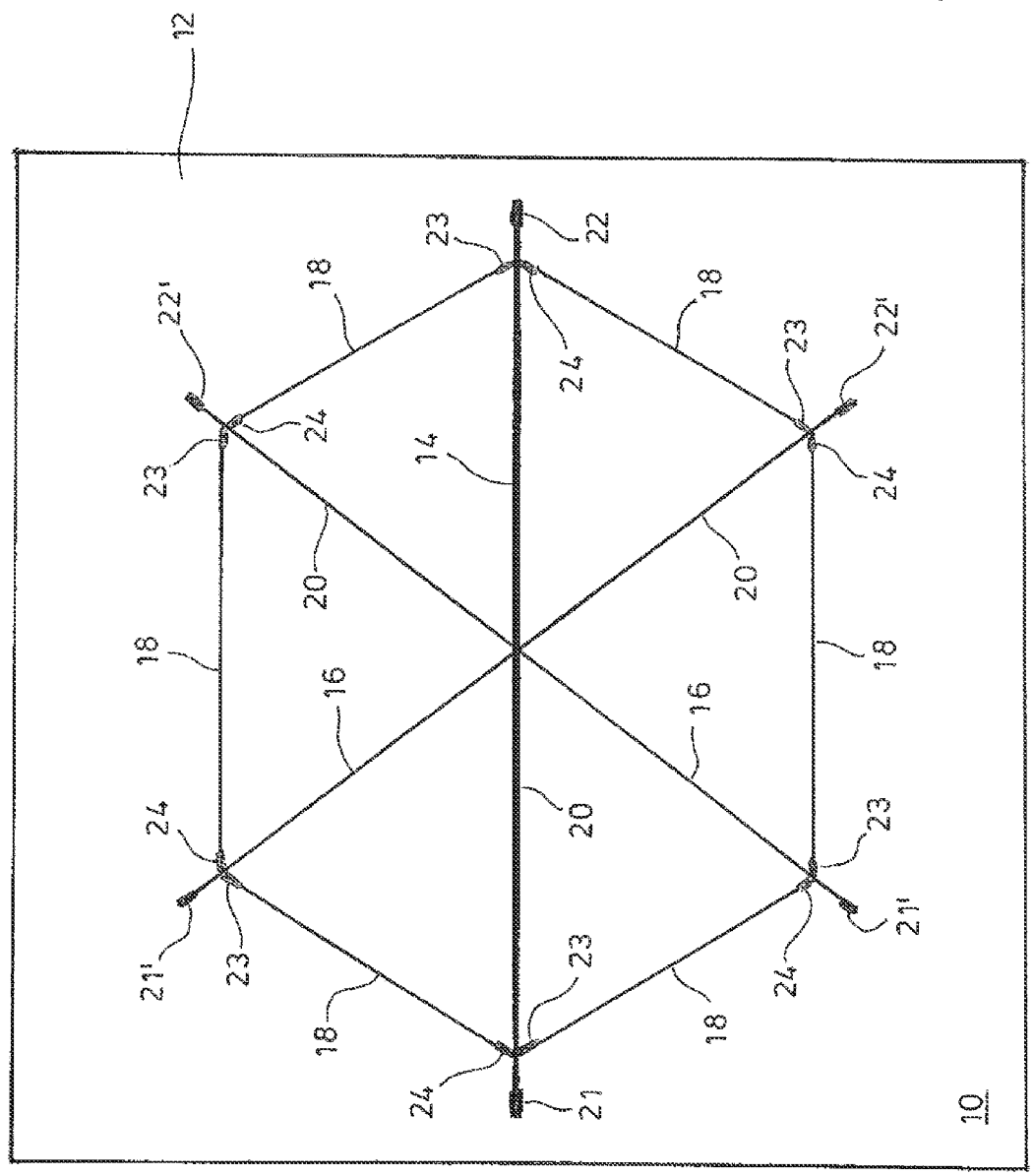

(51) Int. Cl.
*C08J 5/00* (2006.01)
*H05K 13/04* (2006.01)
*A61F 2/00* (2006.01)
*B29C 65/62* (2006.01)
*B29C 65/72* (2006.01)
*B29C 65/02* (2006.01)

(56) References Cited

U.S. PATENT DOCUMENTS

| | | | | |
|---|---|---|---|---|
| 2010/0189764 A1* | 7/2010 | Thomas | ................ | A61F 2/0063 |
| | | | | 424/426 |
| 2011/0307077 A1* | 12/2011 | Pfeiffer | ................ | A61F 2/0045 |
| | | | | 623/23.72 |
| 2013/0218125 A1* | 8/2013 | Stopek | ................ | A61F 2/0063 |
| | | | | 604/500 |
| 2013/0317286 A1* | 11/2013 | Bluecher | ................ | A61L 31/04 |
| | | | | 600/37 |
| 2014/0276999 A1* | 9/2014 | Harms | ................ | A61F 2/0063 |
| | | | | 606/151 |

\* cited by examiner

METHOD OF MANUFACTURING A SURGICAL IMPLANT HAVING A MARKING

CROSS REFERENCE TO RELATED APPLICATIONS

This application claims priority from German Patent Application DE 102014015179.4 filed Oct. 15, 2014 the disclosure of which is hereby incorporated by reference in its entirety.

The invention relates to a method of manufacturing a surgical implant having at least one marking.

Surgical implants which include a marking are well known. For example, when a hernia repair mesh is placed at the site of surgery through a trocar sleeve or through an incision, a marking (e.g. at the center of the mesh) can aid in positioning or orienting the mesh correctly.

EP 1 439 796 B discloses an areal implant comprising a meshlike basic structure and a marking in its central area, wherein a straight marking line runs through this marking.

U.S. Pat. No. 8,579,922 B describes a kit comprising a surgical mesh and sutures. Each of the corner areas of the mesh is marked by a visually coded patch (e.g., coded by color), which is assigned to a correspondingly coded suture.

US 2013/0218125 A discloses an implantable medical device including a surgical mesh and a perforated film positioned on at least a portion of the mesh. The film may include graduated markings.

US 2013/0317286 A describes a surgical implant comprising a bioabsorbable incision reinforcement element, a long-term mesh and a bioabsorbable coating disposed on the mesh. The incision reinforcement element can be provided with an alignment marker including crossed marking lines.

US 2005/0288691 A discloses a hernia patch comprising a sheet formed of one or more layers of a thin flexible material suitable to promote or prevent tissue adherence and a grid formed of intersecting lines. The lines are imprinted on the sheet or made from stitches.

Another surgical implant suitable to hernia repair is known from DE 10 2013 004 486 A. This implant comprises a basic structure including a mesh, which is folded back at the periphery of the implant to form pockets, wherein overlapping parts of adjacent pockets are connected to each other. An absorbable marking pattern is cut from a poly-p-dioxanone film and placed on top of the mesh and an anti-adhesive film (tissue separating layer). After performing a melt-fusing step (lamination by heat), the poly-p-dioxanone material connects the mesh and the anti-adhesive film and provides marking lines.

Common processes for providing and attaching markers to a flexible mesh implant are sewing with a defined and limited stitch length, cut-plotting of a marker film and fixation of the cut film onto the mesh by lamination, printing a marker onto the mesh, or inlaying of colored threads into the textile structure during a knitting process.

However, such processes may affect the properties of an implant mesh (e.g. in terms of flexibility), may be restricted to certain directions or minimum dimensions of markers (e.g. in knitting or cut-plotting processes) or may generally increase manufacturing costs.

The object of the invention is to find a method of manufacturing a surgical implant, in which a flexible areal basic structure can be provided with markings in a convenient, versatile and largely unrestricted way.

This object is achieved by the method of manufacturing a surgical implant as defined in claim 1. Advantageous versions of the invention follow from the dependent claims. Claim 16 relates to a surgical implant manufactured by this method.

In the method according to the invention, a surgical implant is manufactured. The method comprises several steps. A flexible areal basic structure is provided, which has a first face and a second face. At least one linear marking thread is placed, in a floating manner, onto one of the faces of the basic structure. The marking thread is mechanically fixed (e.g. by stitching) to the basic structure at a first location and at a second location, wherein the first location and the second location are spaced from each other. Moreover, the linear marking thread is thermally fixed to the basic structure, in an area between the first location and the second location, by a melt-fusing process.

The method may include at least one further manufacturing step, e.g. before the basic structure is provided, after the marking thread has been fixed, or in between the above steps. Examples for such steps are the application of a barrier film or cutting and folding steps to bring the implant into its final shape.

The term "areal" means that the basic structure is a generally flat structure (e.g. of surgical-mesh material), which may be curved into the third dimension, however. Moreover, the basic structure may be folded (preferably but not necessarily after applying the marking threads), e.g., to form pockets. The implant may consist of the basic structure and the marking threads only, but additional components (e.g. a film attached to the basic structure, etc.) are conceivable as well. A blank of the basic structure may have any shape. A basic structure constituted of more than one part is also possible.

In the method according to the invention, the at least one marking thread is placed onto the basic structure in a floating manner. That means the marking thread is applied with floating fibers, which initially are not attached or interwoven with the basic structure in between the first location and the second location. At the respective first and second locations, the marking threads are fixed to the basic structure, preferably by a sewing process with sewing stitches (e.g. in the edge area of the basic structure). The individual marking threads are designated as linear because they are not used for preparing an extended areal assembly. Preferably, the individual marking threads are placed in a straight manner, in between the respective first and second locations, but without exerting any significant tension onto the basic structure.

By requiring a short set-up time only and very few material, the step of placing the marking threads is highly efficient. There is no waste of material like in a process where a marking pattern is cut out from a film. In the subsequent melt-fusing step, which optionally involves the exertion of pressure, the floated marking threads are melted (or at least transferred into a rather soft state) and converted to a film-like structure so that they may be laminated to the basic structure. For example, they may be bond to a mesh structure by enclosing the mesh filaments, thus preventing delamination. By melting under pressure, the filaments of the marking threads may form a smooth and even surface, which may enhance visibility due to a largely directed reflection of light.

After application of the marking threads, the characteristics of a textile basic structure are generally maintained, which means that the dimensions and the flexibility as well as the textile structure of the basic structure do not significantly change. Moreover, the method according to the invention enables the application of absorbable marking threads onto flexible mesh implants without changing the material characteristics of the remaining implant after the absorption of all absorbable components.

The direction of the marking threads does not depend on any knitting direction of a mesh-like basic structure. That means, marking thread lines can be applied at any angles with respect to a reference direction, e.g. as orthogonal markers.

Generally, the method allows the use of sensitive materials for the basic structure, e.g. of monofilaments which are sensitive to sharp needle tips or of basic material which is sensitive to distortion by the tension of a seam, because the marking threads are placed in a floating manner and any stitching may be restricted, e.g., to peripheral or edge areas.

For example, the first location and the second location of the at least one linear marking thread can be positioned in a peripheral region of the basic structure. It is even possible that parts of the basic structure containing the first location and/or the second location are removed from the implant after thermally fixing the linear marking thread to the basic structure. In that case, the implant does not include any more areas which might have been damaged by mechanically fixing the linear marking thread(s) during manufacture.

In advantageous embodiments of the invention, a linear marking thread or bundle of linear marking threads (forming one marking line) is placed on the first face of the basic structure and, opposite thereto, another linear marking thread or bundle of linear marking threads (forming one marking line) is placed on the second face of the basic structure, wherein both linear marking threads or bundles of linear marking threads are stitched together in respective end areas thereof. Such a process step can be conveniently performed on appropriate state-of-the-art textile machines. In this case, the linear marking thread or bundle of linear marking threads on the first face is securely connected to the linear marking thread or bundle of linear marking threads on the second face, during the melt-fusing step, wherein a mesh-like basic structure may be sandwiched in between. A bundle of linear marking threads is a plurality (i.e. more than one) of linear marking threads generally arranged in parallel to each other.

It has already become evident from the foregoing that a plurality of linear marking threads or bundles of linear marking threads may be provided, on at least one face of the basic structure, to form a pattern of marking lines. Such a pattern can significantly aid a surgeon in correctly positioning and aligning the surgical implant, depending on its shape and the kind of surgery.

The method according to the invention provides an easy way of applying different kinds of marking lines. To this end, in the pattern of marking lines, at least one marking line may comprise a bundle of linear marking threads including more threads than another marking line. In the bundle of linear marking threads, the individual threads are generally aligned in parallel to each other without being intertwined. For example, an axis running through the center of the implant can be marked by a marking line containing more individual threads than other marking lines, wherein it is assumed that the individual threads have the same diameter. In this way, the midline of the implant is highlighted, which facilitates an easy recognition of the orientation of the implant.

A more pronounced marking line can also be achieved by a thread having a greater diameter (in which case the individual filaments of the thread are generally intertwined, e.g. twisted or braided). Generally, a combination of monofilament threads and twisted multifilament threads can be applied in order to achieve a variety of marker types. Every single marking line in a pattern may be adjustable in thickness by the number of applied threads. It is also possible to place linear marking threads on top of each other in order to increase the height of the marker into the third dimension so that a marking line can become palpable. Different colors of the marking lines in a pattern provide another way for an easy distinction between individual marking lines.

The marking lines in a pattern can be used for marking the midline of the implant or an axis perpendicular thereto. It is also possible, however, to mark the periphery or certain areas of the implant. Generally, the method according to the invention is very versatile and permits the provision of many different patterns of marking lines, including well distinguishable marking lines, largely independent of the size of the implant.

If the finished surgical implant has a generally polygonal shape, the pattern of marking lines may include marking lines along the periphery of the implant and/or marking lines connecting opposite corners of the implant and crossing each other in a center area of the implant. In an example for such an implant, the basic structure (e.g., a surgical mesh) is folded back at the periphery of the implant to form pockets, wherein overlapping parts of adjacent pockets are connected to each other. DE 10 2013 004 486 A discloses a surgical implant of this kind. The markings described therein form a somewhat different pattern, however. Moreover, they are shaped from a film structure connected to the basic structure, or they are embroidered or sewn on the basic structure, which does not involve the advantages of the present invention.

In a hexagonal surgical implant, for example, the pattern of marking lines comprises a prominent midline and less prominent grid markers. The grid markers run about the periphery of the implant, and they connect opposite corners of the implant, i.e. those corners not connected by the midline. Alternatively, one grid marker line runs through the center of the implant, but crosses the midline at a right angle. In the example, each of the grid marker lines includes two pairs of parallel linear marking threads, wherein each pair is composed of one linear marking thread ("needle thread") running on the first face of the basic structure and one linear marking thread ("bobbin thread") running on the second face of the basic structure. Similarly, the midline contains eight pairs of parallel linear marking threads so that it is more pronounced than the grid markers. Each pair of parallel threads is positioned across the basic structure using a floated needle and bobbin thread. The ends of the threads of each pair are stitched together.

The at least one marking thread may be provided as a monofilament or as a multifilament, e.g. as a twisted multifilament. In advantageous embodiments, the marking thread is absorbable and has a melting temperature lower than that of at least one constituent of the basic structure, which generally facilitates the melt-fusing process. A preferred material is poly-p-dioxanone, in particular dyed (e.g. violet) poly-p-dioxanone. Any combinations of materials and properties for different marking threads are possible as well.

As already indicated before, the basic structure may comprise a surgical mesh, e.g. a surgical mesh as used in hernia repair. In advantageous embodiments, the basic structure is macro-porous, e.g. having a pore size of at least 1 mm. It may be a light-weight construction having an areal weight of less than 50 g/m$^2$, but it could also be heavier. The basic structure can comprise, e.g., a warp-knit, a weft-knit, a crochet-knit and/or a woven fabric, but also a perforated film. If it includes filaments, the filaments may be bioabsorbable or non-absorbable, and the filaments can comprise mono-filaments and/or multi-filaments (including multi-filaments made from different materials). Tape yarns and/or drawn film tapes are conceivable as well.

The basic structure may comprise absorbable material, non-absorbable material or a combination of absorbable material and non-absorbable material. For example, a mesh-like basic structure may be warp-knitted from threads which are twisted from absorbable and from non-absorbable filaments.

Advantageous materials for the basic structure, e.g. a basic structure comprising a surgical mesh, include, e.g., polypropylene, fluorinated polyolefines, blends of polyvinylidene fluoride and copolymers of vinylidene fluoride and hexafluoropropene (e.g. Pronova™, Poly(Hexafluoropropylene-VDF) material of Ethicon), which are all non-absorbable. Examples for absorbable materials are poly-p-dioxanone (PDS), copolymers of glycolide and lactide, in particular copolymers of glycolide and lactide in the ratio 90:10 (e.g. Vicryl™, polyglactin 910, synthetic absorbable filaments of Ethicon), and copolymers of glycolide and ε-caprolactone (e.g. Monocryl™, Ethicon). Other biocompatible materials for the basic structure, as generally known in the art, are conceivable as well. Moreover, the basic structure can comprise a mixture of different materials, including a mixture or absorbable and of non-absorbable materials.

In advantageous embodiments, the basic structure comprises a tissue separating layer. That means the tissue separating layer is already present at the basic structure during the step of providing the flexible areal basic structure, i.e. before placing the at least one linear marking thread. In other versions of the method according to the invention, a tissue separating layer is attached to the basic structure after at least one linear marking thread has been applied to the basic structure.

For example, in the case of the above-mentioned polygonal hernia repair implant comprising pockets, a tissue separating layer or film (anti-adhesive film) may be located at the face of the basic structure pointing away from the pockets, i.e. on the visceral side of the implant. The tissue separating layer resists and prevents ingrowth of bodily tissue into a meshlike structure and acts anti-adhesive. Preferably the tissue separating layer is absorbable so that it exhibits its effect during the initial healing period, when this is important. The tissue separating layer may cover the area or part of the area of the basic structure. For example, on the initial basic structure, it may extend beyond the outer polygonal periphery of the implant, where the tissue separating layer is folded back together with the material (flaps) of the pockets. Preferably, less than 50% of the area of the pocket flap material is covered by the tissue separating layer. In this way, the edges of the surgical implant are also protected from generally undesired adhesion to bodily tissue.

Suitable materials for the tissue separating layer are, e.g. poly-p-dioxanone (PDS), ε-caprolactone, copolymers of glycolide and ε-caprolactone (e.g. Monocryl™ film of Ethicon), oxygenized regenerated cellulose (ORC), collagens or combinations thereof, but other anti-adhesive and bio-compatible materials known in the art can be considered as well. The tissue separating layer can have any thickness in the range of, e.g., 2 μm to 1000 μm. Typical thicknesses are in the ranges of 5 μm to 100 μm and preferably of 8 μm to 30 μm.

The tissue separating layer or film can be connected, e.g., to mesh material of the basic structure over the full surface of the tissue separating layer or over part of the surface of the tissue separating layer, e.g. by laminating, welding, gluing and/or sewing (e.g., lamination of a bi-layer film comprising a Monocryl™ film and a PDS film). Additional material used for laminating, gluing and/or sewing may be permanent (non-absorbable), absorbable or partially absorbable.

In the following, the invention is described in further detail by means of an embodiment. The drawings show in FIG. 1 a top view illustrating initial steps in an embodiment of a method of manufacturing a surgical implant, FIG. 2 a top view illustrating further steps in that embodiment, and FIG. 3 a three-dimensional view showing the finished implant manufactured according to that embodiment.

The method of manufacturing a surgical implant starts with the step of providing a flexible areal basic structure 10, see FIG. 1. In the embodiment, the basic structure 10 is initially presented as a rectangular piece of a conventional surgical mesh. This surgical mesh may be warp-knitted, e.g., from threads comprising polypropylene and poly-p-dioxanone (PDS). To this end, e.g., monofilaments of polypropylene and PDS can be used as different threads in the warp-knitting pattern, or a twisted thread made from a polypropylene filament and a PDS filament can be used. The basic structure 10 has a first face 12, which is visible in FIG. 1, and a second face on the opposite side.

In a next step of the method, a midline 14, two additional central marking lines 16 and a total of six peripheral marking lines 18 are placed on the piece of surgical mesh serving as basic structure 10. The midline 14 and the additional marking lines 16 and 18 form a pattern of marking lines and are made from linearly aligned marking threads (linear marking threads) 20, as explained in the following.

The midline 14 is prepared by a plurality of pairs of parallel marking threads 20, wherein each pair is composed of one marking thread ("needle thread") running on the first face 12 of the basic structure 10 and one marking thread ("bobbin thread") running on the second face of the basic structure 10. Each pair of parallel marking threads 20 is positioned across the basic structure 10 by using a floated needle and bobbin thread, a technique well-known in the art as such. The ends of the marking threads 20 of each pair are stitched together at a first location 21 and at a second location 22. In the embodiment, e.g., dyed (violet) PDS monofilaments can be used as the material for the marking threads 20.

Thus, the plurality or bundle of pairs of marking threads 20 placed in this way forms a pronounced midline 14, which is fixed at the first location 21 and at the second location 22, but just after this step of the method is not yet fixed in between the first location 21 and the second location 22.

The additional central marking lines 16 are placed in an analogous manner and fixed by stitching to the basic structure 10 at respective first locations 21' and second locations 22'. Similarly, the peripheral marking lines 18 are applied in a floating manner as well and mechanically fixed by stitching at respective first locations 23 and second locations 24. In contrast to the midline 14, the additional central marking lines 16 and the peripheral marking lines 18 contain less pairs of marking threads 20 so that they appear to be less pronounced than the midline 14.

Figure 2:
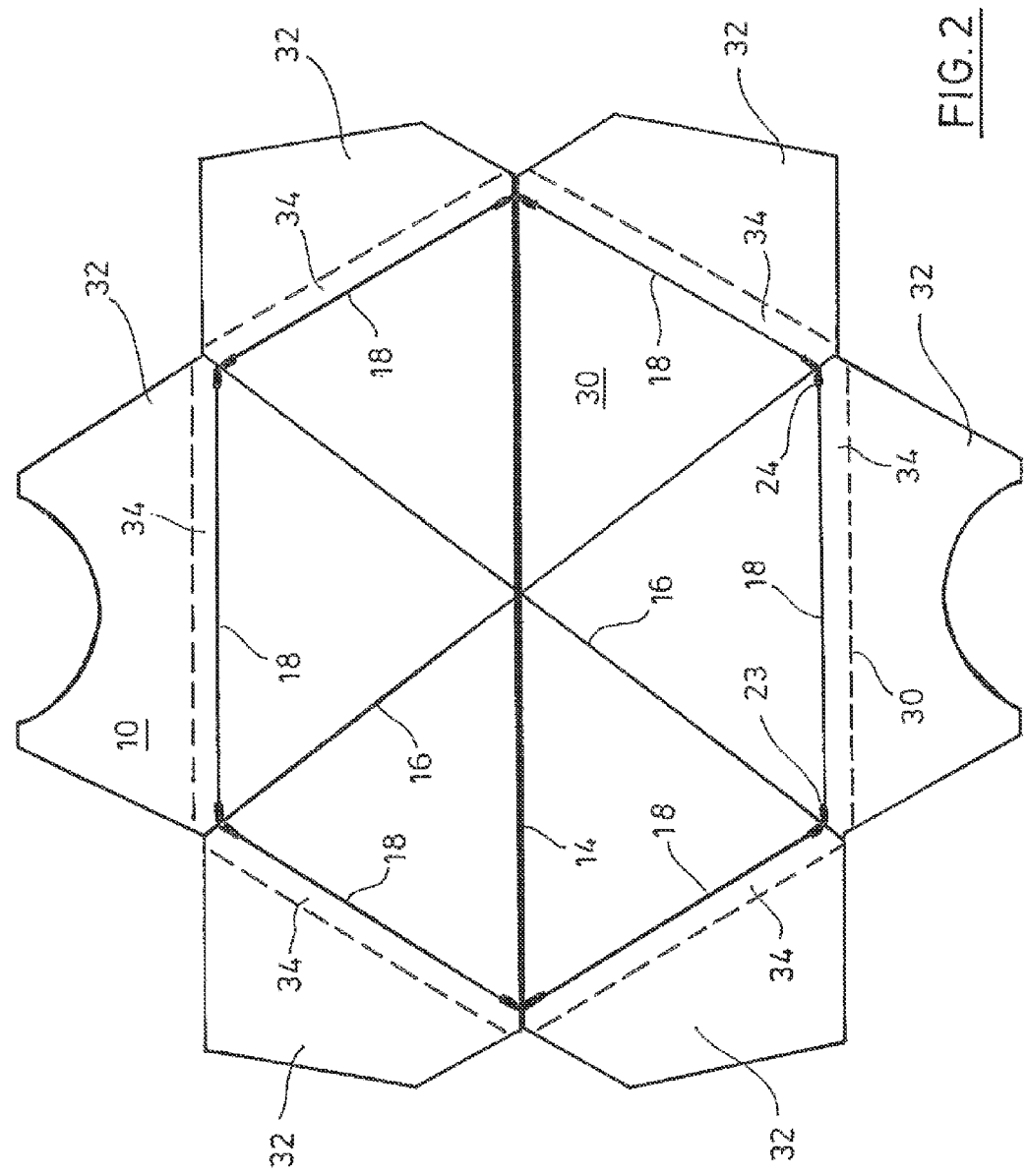

In a further step of the method, a tissue separating layer 30 prepared as, e.g., a film made of the absorbable material Monocryl™ (a copolymer of glycolide and ε-caprolactone marketed by Ethicon) is placed on top of the first face 12 of the basic structure 10, thus also covering the midline 14, the additional central marking lines 16 and the peripheral marking lines 18. In the embodiment, the tissue separating layer 30 has a hexagonal shape and is slightly greater than the pattern provided by the peripheral marking lines 18, to which the tissue separating layer 30 is symmetrically aligned, see FIG. 2. In FIG. 2, the tissue separating layer 30 is represented by dashed lines.

In a next step of the method, the tissue separating layer 30 is pressed against the basic structure 10, while applying heat. This results in a full lamination of the tissue separating layer 30 with the basic structure 10 and the marking threads 20 in the pattern of marking lines consisting of the midline 14, the additional central marking lines 16 and the peripheral marking lines 18, because the PDS contained in the basic structure 10 and the marking threads 20 melts or gets very soft. In this way, the marking threads 20 are thermally fixed to the basic structure 10 in the areas between the respective first locations 21, 21', 23 and second locations 22, 22', 24 by a melt-fusing process. This fixation is very reliable because the mesh material of the basic structure 10 is embedded in the PDS material of the marking threads 20 from the side of the first face 12 of the basic structure 10 and also from the opposite side. Moreover, the tissue separating layer 30 is attached to the basic structure 10 virtually over its full area, due to the melt-fusing effect of the PDS component of the basic structure 10. The melting temperature of PDS is lower than that of polypropylene and Monocryl™.

In a next step of the method, the material of the rectangular piece of the basic structure 10 not required anymore for the finished implant is removed in a cutting process. In this way, the peripheral line of the shape shown in FIG. 2 is formed. The first locations 21 and 21' as well as the second locations 22 and 22' of the midline 14 and the additional central marking lines 16, respectively, are removed in the cutting process. Small corner areas of the tissue separating layer 30, which is initially hexagonal, are removed as well, see FIG. 2.

In this state, the basic structure 10 comprises a total of six pocket flaps 32, see FIG. 2. The tissue separating layer 30 extends somewhat beyond the peripheral marking lines 18, thus forming edge zones 34, but the residual area of the pocket flaps 32 is free of the tissue separating layer 30.

In a next step, the pocket flaps 32 are folded back onto the second face of the basic structure 10 along folding lines running through the edge zones 34 in parallel to the respective peripheral marking lines 18 and close to the latter.

Figure 3:
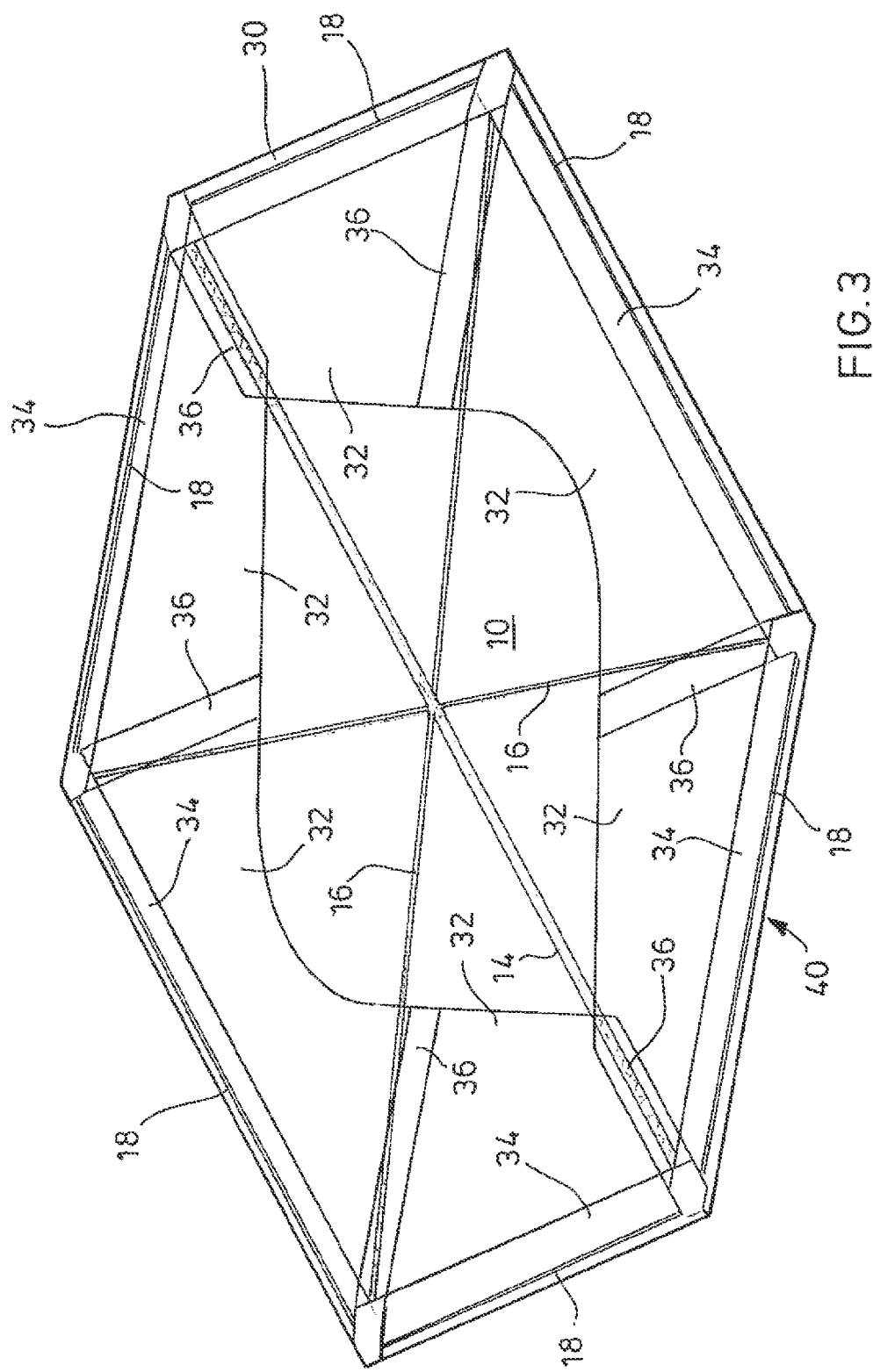

FIG. 3 shows the resulting structure in a three-dimensional view, after it has been turned around and the pocket flaps 32 are visible again. In overlapping parts 36, the edges of adjacent pocket flaps 32 are melt-fused together. In this way, a total of six pockets is formed, one assigned to each pocket flap 32, so that a user of the implant can grasp into the pockets, which facilitates the handling of the implant. In the embodiment, the overlapping parts 36 are not attached to the opposite side of the basic structure 10. In FIG. 3, the finished surgical implant is designated by 40.

The tissue separating layer 30 extends from the visceral side of the basic structure 10 (pointing downwards in FIG. 3) around the peripheral edge of the implant 40 up to the parietal side (pointing upwards in FIG. 3), where it covers a narrow zone close to the peripheral edge. In this way, the visceral side and the peripheral edge zone of the implant 40 exhibit an anti-adhesive effect.

FIG. 3 illustrates that, due to the presence of the midline 14, the additional central marking lines 16 and the peripheral marking lines 18, the orientation, the center and the periphery of the implant 40 can be easily recognized.

EXAMPLE

A surgical implant was manufactured as generally explained before by means of FIGS. 1 to 3.

The surgical mesh of the basic structure was fabricated from a combination of polypropylene and PDS filaments. For the marking threads, PDS monofilament threads of 109 μm (4.3 mils) diameter, dyed violet, were used. The midline was prepared from eight pairs of parallel floated needle and bobbin threads which were stitched together in the edges (first and second location). Similarly, for each of the additional central marking lines and each of the peripheral marking lines, two pairs were used. The tissue separating layer was made from a Monocryl™ film of a thickness of approximately 10 μm. The Monocryl™ film was fully laminated to the mesh and the marking threads by heat-fusing the PDS component of the mesh and the marking threads to the Monocryl™ film. Finally, the implant was cut to shape, folded and finished, as described above with respect to FIGS. 2 and 3.

The invention claimed is:

1. A method of manufacturing a surgical implant, comprising the steps of
   providing a flexible areal basic structure having a first face and a second face, placing at least one linear marking thread in a floating manner, onto one of the faces of the basic structure and mechanically fixing the marking thread to the basic structure at a first location and at a second location which are spaced from each other,
   thermally fixing the linear marking thread to the basic structure in an area between the first location and the second location by a melt-fusing process.

2. A method according to claim 1, characterized by at least one further manufacturing step.

3. A method according to claim 1, characterized in that a linear marking thread or bundle of linear marking threads is placed on the first face of the basic structure and, opposite thereto, another linear marking thread or bundle of linear marking threads is placed on the second face of the basic structure, wherein both linear marking threads or bundles of linear marking threads are stitched together in respective end areas thereof.

4. A method according to claim 1, characterized in that the first location and the second location of the at least one linear marking thread are positioned in a peripheral region of the basic structure.

5. A method according to claim 4, characterized in that parts of the basic structure containing at least one of the first location and the second location are removed from the implant after thermally fixing the linear marking thread to the basic structure.

6. A method according to any claim 1, characterized in that a plurality of linear marking threads or bundles of linear marking threads is provided, on at least one face of the basic structure, to form a pattern of marking lines.

7. A method according to claim 6, characterized in that, in the pattern of marking lines, at least one marking line comprises a bundle of linear marking threads including more threads than another marking line.

8. A method according to claim 6, characterized in that the finished surgical implant has a generally polygonal shape, wherein the pattern of marking lines includes at least one of the following groups of marking lines: marking lines along the periphery of the implant, marking lines connecting opposite corners of the implant and crossing each other in a center area of the implant.

9. A method according to claim 8, characterized in that the basic structure is folded back at the periphery of the implant to form pockets, wherein overlapping parts of adjacent pockets are connected to each other.

10. A method according to claim 1, characterized in that the basic structure comprises a surgical mesh.

11. A method according to claim 10, characterized in that the basic structure comprises a tissue separating layer.

12. A method according to claim 10, characterized in that a tissue separating layer is attached to the basic structure already provided with the at least one linear marking thread.

13. A method according to claim 1, characterized in that the at least one marking thread comprises at least one of the following properties: provided as monofilament, provided as multifilament, provided as twisted multifilament, being absorbable, having a melting temperature lower than that of at least one constituent of the basic structure, made of dyed poly-p-dioxanone.

14. A method according to claim 1, characterized in that the basic structure comprises absorbable material.

15. A method according to claim 1, characterized in that the basic structure comprises non-absorbable material.

* * * * *